United States Patent
Pellegretti et al.

(10) Patent No.: US 6,652,460 B2
(45) Date of Patent: Nov. 25, 2003

(54) METHOD FOR ULTRASONIC IMAGING, PARTICULARLY OF MOVING BODIES, SUCH AS SURGICAL UTENSILS, TISSUES, FLOWS, OR THE LIKE

(75) Inventors: Paolo Pellegretti, Genoa (IT); Mauro Fabiano, Genoa (IT); Marco Merlanti, Arenzano (IT)

(73) Assignee: Esaote, S.p.A., Casale Monferrato (IT)

( * ) Notice: Subject to any disclaimer, the term of this patent is extended or adjusted under 35 U.S.C. 154(b) by 0 days.

(21) Appl. No.: 09/850,627

(22) Filed: May 4, 2001

(65) Prior Publication Data

US 2001/0044580 A1 Nov. 22, 2001

(51) Int. Cl.$^7$ ................................................ A61B 8/00
(52) U.S. Cl. ........................ 600/443; 600/437; 600/454; 600/455
(58) Field of Search .................... 600/437–472

(56) References Cited

U.S. PATENT DOCUMENTS

| | | | | |
|---|---|---|---|---|
| 4,109,642 A | * | 8/1978 | Reid et al. ................... 600/457 |
| 5,109,858 A | * | 5/1992 | Nishiyama et al. ......... 600/455 |
| 5,355,887 A | * | 10/1994 | Iizuka et al. ................ 600/440 |
| 5,415,171 A | * | 5/1995 | Goh et al. ................... 600/443 |
| 5,453,575 A | | 9/1995 | O'Donnell et al. .... 128/662.06 |
| 5,482,044 A | * | 1/1996 | Lin et al. .................... 600/453 |
| 5,522,392 A | | 6/1996 | Suorsa et al. .......... 128/661.08 |
| 5,548,561 A | | 8/1996 | Hussain et al. ................ 367/7 |
| 5,622,174 A | * | 4/1997 | Yamazaki .................... 600/453 |
| 5,718,229 A | | 2/1998 | Pesque et al. ............... 128/443 |
| 5,820,561 A | * | 10/1998 | Olstad et al. ................ 600/441 |
| 5,873,830 A | * | 2/1999 | Hossack et al. ............. 600/447 |
| 5,961,461 A | * | 10/1999 | Mo et al. ..................... 600/443 |
| 6,010,456 A | * | 1/2000 | Rhyne ......................... 600/447 |
| 6,013,031 A | * | 1/2000 | Mendlein et al. ........... 600/442 |
| 6,048,312 A | * | 4/2000 | Ishrak et al. ................ 600/443 |
| 6,083,168 A | * | 7/2000 | Hossack et al. ............. 600/443 |

FOREIGN PATENT DOCUMENTS

GB  2 328 745  3/1999 ............ A61B/8/00

* cited by examiner

*Primary Examiner*—George Manuel
*Assistant Examiner*—William C. Jung
(74) *Attorney, Agent, or Firm*—Woodard, Emhardt, Moriarty, McNett & Henry LLP (57) ABSTRACT

A method for ultrasonic imaging, particularly of moving bodies, such as surgical utensils, tissues, flows, or the like, which includes the following steps:—Periodically emitting ultrasonic pulses along a predetermined view line and with a predetermined repetition rate through one or more transducers;—Receiving the echoes produced by the body and/or the tissues or flows and transforming them into echo signals;—Processing the echo signals for extracting information therefrom and for generating an image based on such information. According the invention, the following steps are additionally provided:—determining a real time vector difference between the echo signals of two pulses successively emitted at predetermined time intervals;—using said difference signal as an information signal for ultrasonic imaging.

22 Claims, 5 Drawing Sheets

METHOD FOR ULTRASONIC IMAGING, PARTICULARLY OF MOVING BODIES, SUCH AS SURGICAL UTENSILS, TISSUES, FLOWS, OR THE LIKE

BACKGROUND OF THE INVENTION

The invention pertains to a method for ultrasonic imaging, particularly of moving bodies, such as tissues, flows, or the like, which includes the following steps:

Periodically emitting ultrasonic pulses along a predetermined view line and with a predetermined repetition rate through one or more transducers;

Receiving the echoes produced by the body and/or the tissues or flows and transforming them into echo signals;

Processing the echo signals for extracting information therefrom and for generating an image based on such information.

Particulalrly the invention relates to an apparatus for implementing and using the method and to an apparatus for detecting intraoperative surgical instruments and calcifications or similar biological structures The ultrasonic imaging technique consists in generating an ultrasonic pulse beam, having frequencies in the RF range, from a set of aligned emitting transducers to illuminate or soundproof a definite section of a body or of a body part to be examined. As the individual pulses propagate in the body according to a predetermined penetration depth, as determined by their nature and by the nature of the body being examined, they are reflected by the structures forming the body and generate reflected echoes, which are detected by detectors and transformed into echo signals. The different structures or types of tissues encountered by the illuminating pulses while the latter propagate in the body along a propagation axis or view line produce changes in the emitted carrier, in the form of amplitude modulations or phase variations. These changes are the information to be extracted by the echo signals to obtain the ultrasonic image.

In the simplest form of ultrasonic image, the so-called B-mode image, a black and white image is generated, in which the different tones of gray, black and white are related to the intensity or the amplitude of the received echo signal. Processing requires synchronization, on a predetermined time base, of the emitted pulses and of the received echo signals to accurately reconstruct the zones wherefrom the echoes arrive along the propagation line, in accordance with the propagation of the illuminating pulse and further to allow correlation of the echo signals to their respective illuminating pulse-emitting transducers.

Therefore, the information contained in the echo signals may be interpreted either with respect to amplitude modulations of the illuminating pulse, as in the so-called B-Mode, or with respect to phase variations, such as in the so-called Doppler, Power Doppler, Color Doppler, or the like.

From surgical point of view there is a need to control position and displacement of intraoperative utensils in the human or animal body by means of a non invasive technique which is capable of giving an intelligible image of the region where the intraoperative utensil is placed.

From the diagnostic point of view, there is the need of noninvasively imaging particular tissue types, such as for example calcifications or similar biological structures in the human and animal body. This kind of tissues are not simple to be scanned with ultrasound techniques.

From the diagnostic point of views there is also a very high interest in the ultrasonic imaging of flows in the human bodies, particularly of blood flows. The problem consists in that most of the physiological liquids, such as blood, urine, bile, cyst contents, etc. are anechogenic, i.e. transparent, or only partially reflect ultrasounds.

Thus, ultrasonic imaging with the conventional B-Mode method is not feasible and produces poor, unusable results. Therefore, several techniques have been implemented to detect flows, particularly blood flows, with ultrasound apparati, the so-called Doppler, Power Doppler, Color Doppler techniques, or the so-called Harmonic Imaging technique, in which the echo signal is examined with respect to its harmonics. These prior art techniques require both processing in the frequency or phase domain, which add a considerable processing burden, and the use of the so-called contrast agents, consisting of microbubbles, which, when injected in spontaneous flows, have a hyperechogenic behavior.

Actual techniques for imaging of physiological flows are not optimized for imaging of surgical apparatus or for biological structures such as calcifications. Indeed imaging apparatus and techniques normally are arranged and chosen in such a way as to avoid the contributes of the scattered ultrasonic beams due to the presence in the region being scanned of surgical intraoperative utensils or biological structures such as calcifications.

The present invention has the object to provide a method for ultrasonic imaging, particularly of moving bodies, such as intraoperative utensils, tissues, flows or the like, which allows fast real time and simple imaging of the said utensils and or tissues and also real time imaging of body flows even without using contrast agents, without excluding the combined use thereof, and at the same time is highly sensitive to movement, thereby allowing to considerably simplify processing of echo signals for extracting and displaying information.

The invention achieves the above purposes by providing a method for ultrasonic imaging, particularly of moving bodies, such as surgical inytraoperative utensils, tissues, flows, or the like, which includes the following steps:

determining a real time vector difference between the echo signals of two pulses successively emitted at predetermined time intervals;

using said difference signal as an information signal for ultrasonic imaging.

Therefore, a direct and vector difference between the received RF echo signals is determined, which involves suppression of the contributions or portions of the echo signals produced by the stationary parts of the body, tissues or the like, whereas the portions of the echo signals produced by moving bodies, such as intraoperative surgical utensils, calcifications or the like and/or tissues or elements, such as red blood cells, etc. give non-zero contributions due to displacement of said moving bodies or parts.

Processing of the difference signal for imaging is performed as in conventional ultrasonic imaging techniques.

The method of the invention allows ultrasonic imaging of moving bodies, particularly of spontaneous body flows, i.e. of blood flows or the like, without using radiopaque agents.

The method of the invention is highly sensitive to movement, therefore it can generate images of very slow or low flow rate flows or of parts which perform micromovements.

The resulting images have a high definition and a considerable level of contrast and, in combination with high sensitivity to movement and micromovement of bodies in the operating range of the probe, they allow to display and monitor movements of invasive surgical instruments, such as microinstruments, intraoperative probes, needles, etc. better than the other prior art ultrasonic methods.

Thanks to the high sensitivity of the method, ultrasonic images may be also obtained from biological structures which are highly echogenic, but perform little or very slow movements, i.e. perform even slow micromovements, such as calcifications or breast cancer formations.

In order to adapt the imaging technique according to the invention to the different kind of analysis needed, the difference RF signal is further treated by non linear filtration of the signal components which are not of interest for the specific analysis and may hinder correct evaluation of the interesting part of the echo signals.

Indeed high echogenic tissues or materials may contribute very significatively to the echo signals and with such an high response that the contribution to the signal due to the tissue of interest is reduced to a very insignificant part of the signal.

Due to the said sensitivity of the method according to the invention to micromovements, high ecogenic materials, such as in the case of surgical utensils or calcifications may generate some sort of intensity flashes that let the contribution of less ecogenic tissues practically disappear This may be a problem when the flow to be detected, e.g. blood flow, is particularly anechogenic, and is surrounded by hyperechogenic, i.e. hyperreflecting or hyperdense tissues, with respect to ultrasonic pulses. In this case, the micromovements between the probe and said hyperechogenic tissues (e.g. walls of blood vessels or tissues of organs), give a non-zero difference signal, whose intensity is much higher than the contribution, for instance, of the blood flow or other flows or moving bodies, which are less echogenic or even classifiable as anechogenic, whereby the signal generated by the flow has a limited level with respect to the signal produced by echogenic or hyperechogenic tissues. In this case, the method may fail to image said flows.

From one point of view the method according to the invention allows to rapidly scan and image intraoperative surgical utensils and biological structures such as calcifications or breast cancer by executing a non linear filtering of the received difference echoes signals which filtering cut away the signal below a certain intensity level, thus using for reconstructing the image merely the high intensity difference signals. This is exactly the contrary which is done in the actual known techniques, since in these actual techniques this high signal components are filtered away or reduced in intensity.

On the other hand in order to image physiological flows the same non linear filtering process is used to neutralize signal flashes generated by relative micromovements between the prove and the echogenic or hyperechogenic tissues which surround the flows whereof ultrasonic imaging is desired and/or by intraoperative utensils or by the said biological structures as calcifications. In this case the part of the difference signal used for generating the image is the part below the above mentioned intensity threshold. In this case there are cut away the difference signal parts above the said intensity threshold.

Particularly for both cases, the above non linear filtering is based on the fact that, in the so-called B-Mode echo signal processing (generally known to the skilled in the art and used substantially in all ultrasound machines) the flows generally composed of anechogenic components give much lower signal powers or intensities than echogenic and hyperechogenic tissues.

Therefore, a maximum intensity threshold may be defined, above which the components of the difference signal between two successive echoes are drastically attenuated or set to zero, while the components of the difference signal between successive echoes whose intensity or power is below said threshold are retained, or vice versa depending on the kind of analysis is being executed.

With reference to a further characteristic of the invention, it is possible to define more than one unique intensity threshold of the echo difference signals. In this case, in addition to a maximum threshold, a minimum threshold may be defined, i.e. a window, whereby the signals or signal components included in said intensity window may be alternatively retained, or drastically reduced or set to zero, and the components of the difference signal whose intensity is outside said window or range are strongly attenuated or set to zero or alternatively retained.

According to the above feature of setting more than one threshold different combination of intensity components of the difference echoes signals may be used for reconstructing an image, being thus able to add information to the image reconstructed relating to different tissues which may surround the object scanned and whose image is required.

By further applying weights to the signal components which are due to tissues or objects which are not o principal interest of imaging it is possible to scale the contribution of this tissues or bodies in order to enhance the image of the relevant object and give at the same time a view of its position in the region scanned relatively to other tissues or objects, which will appear in the image with a level of intensity adaptable to the desires of the user.

Besides determining the maximum signal intensity threshold above which echo signals hate to be set to zero or retained for constructing the image, a limited-intensity imaging of the background of the whole section may be allowed, i.e. of the zone in the proximity or surroundings of the spontaneous flow, particularly the blood flow.

In this case, from a first echo signal, only a portion of the subsequent echo signal is subtracted. By this arrangement, contribution by stationary tissues or parts of the body structure is not completely suppressed but generates a signal greater than zero related to said stationary structures or tissues, hence a limited-intensity image of the zones surrounding the intraoperative utensil, the biological structure or the flow under examination.

Thanks to this arrangement, it is not only possible to obtain real time images of intraoperative utensils, radiopaque biological structures and/or anechogenic flow, but also of the tissues or regions surrounding such flow, concurrently illuminated by the pulses emitted by the transducer.

SUMMARY OF THE INVENTION

It is important to understand that the present invention uses a signal components of the echo signals which normally are cut or filtered away or strongly attenuated as being considered of damage to the reconstruction of an image. It is also important to consider the fact that the particular non linear filtering allows parallel evaluation of the signal components above and below the intensity threshold thus allowing a parallel real time imaging of ecogenic bodies or tissues executing micromovements relating to the ultrasound probe and of not echogenic bodies or tissues executing spontaneous displacements or flows in the region scanned. From the above description it appears clearly that the method according to the invention allows imaging of a intraoperative utensil and at the same time of blood flow in the vicinity of the utensil, allowing to combine these two images and further to combine these images alone or together with an image of the surrounding tissues.

Defining more than one threshold of intensity it is further possible to set more levels of combination and of scaling of the combined images which may be obtained, controlling their contribution to the final image in a simple way.

Furthermore it is important to note that according to the filtering method suggested by the present invention, i.e. a non linear filtering due to a signal cut-off by means of a discrimination threshold, it is possible to implement the method comprising the difference and anti-clutter filtering of the signals using only two shots or bursts for each vector. On the contrary the actual techniques using digital filters of the type denominated FIR, need in their most simple embodiments at least three shots or bursts for each vector. This feature allow to operate with the method according to the invention at higher frame rates than according to the actual methods.

The invention also pertains to an apparatus for implementing said method, which includes a probe for emitting RF ultrasonic pulses, generally consisting of a set of transducers aligned on at least one line;

transducers for receiving the echo signals reflected by the body under examination while the illuminating ultrasonic pulses propagate therein;

processing means, including means for generating an image from the received signals;

means for determining a difference signal between two received echo signals.

Moreover, the invention provides means for generating a threshold for filtering the signal useful for imaging, which is related to signal intensity.

Weighting means may be provided for the second signal which is subtracted from the first echo signal, to generate a partial subtraction of said second signal from the first echo signal.

The characteristics of the invention and the advantages derived therefrom will appear more clearly from the following description of a non limiting embodiment, illustrated in the annexed drawings.

DESCRIPTION OF THE PREFERRED EMBODIMENT

Referring to the figures, the ultrasonic imaging method according to the invention provides the generation of ultrasonic "illuminating" pulses I1, I2, I3, . . . , In by a probe 1 provided with n transducers T1, T2, T3, . . . , Tn with a predetermined repetition rate.

Figure 1:
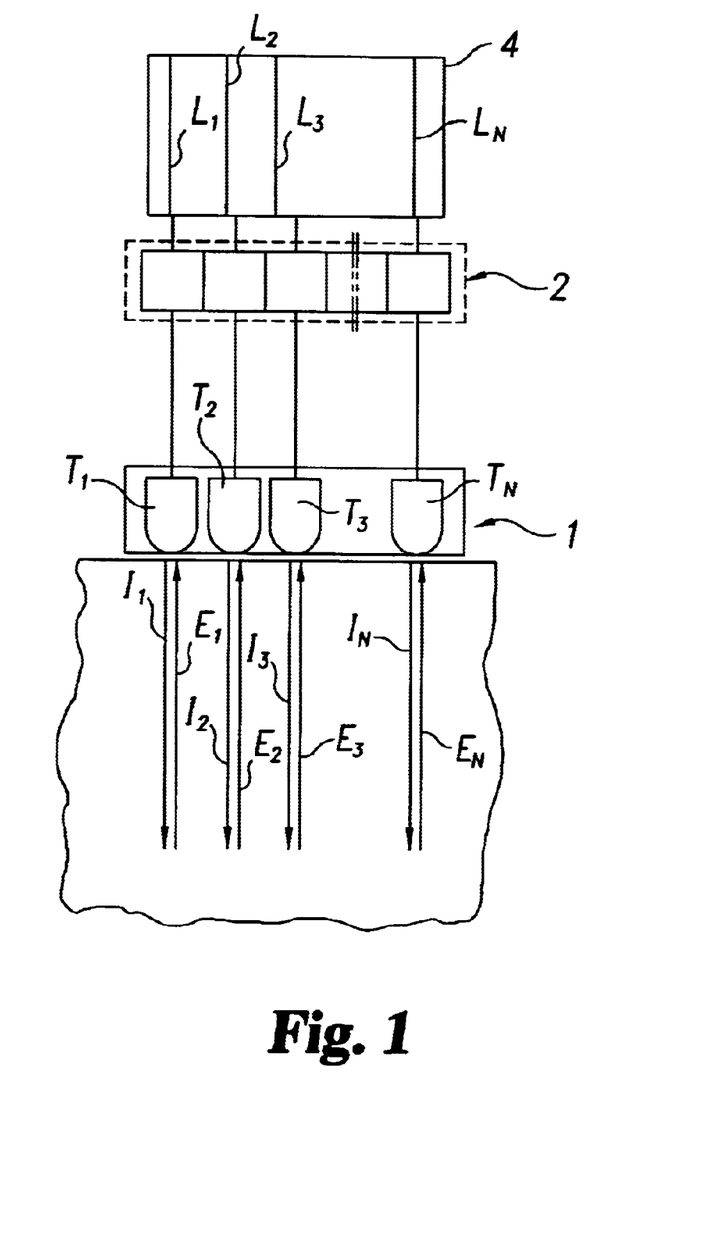
FIG. 1 is a schematic view of an ultrasound apparatus.
Figure 2:
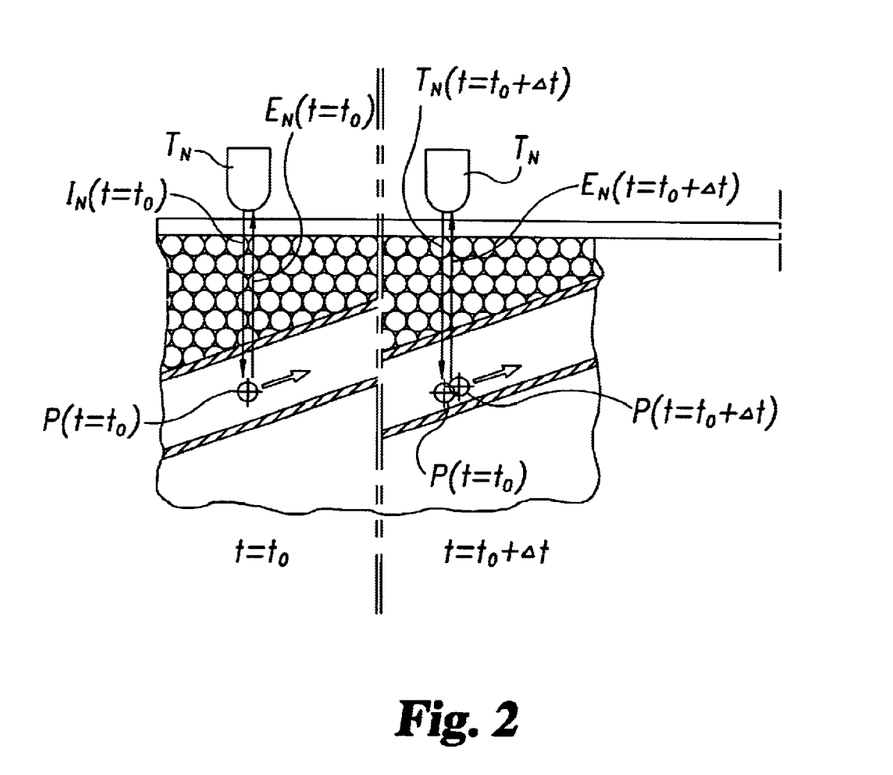
FIG. 2 shows a schematized condition, in the method of the invention, at times t and t+dt.

This situation is shown in FIG. 2, with reference to a single transducer Tn. This figure shows the transducer at the moment t=t0 and at the moment t=t0+dt.

The transducer Tn emits a pulse In(t=t0) at time t0 and a subsequent pulse In(t=t0+dt) at a subsequent time. According to the invention, a subtraction is performed between the echoes En(t=t0) of the illuminating pulse In (t=t0) and En(t=t0+dt) of the illuminating pulse I(t=t0+dt), thereby obtaining the difference signal Diff. (n, t0, t0+dt).

$$Diff(n, t0, t0+dt)=En(t0)-En(t0+dt)$$

When stationary tissues are present, i.e. tissues which do not move relative to the probe 1, their contributions to the echo signals En(t0) and En(t0+dt) suppress each other, whereas the contributions to echo signals by moving parts of the body, such as spontaneous body flows, especially blood flows, or else as for example micromovements or displacements of intraoperative surgical utensils or biological structure like calcifications or similar, do not suppress each other, thereby substantially changing reflection conditions in the interval between two successive illuminating pulses In(t0) and In(t0+dt) This is shown in FIG. 2 with the target particle P inside a vessel. At time t=t0, the particle is in the position P whereas, at time t=t0+dt, it is displaced, thereby generating a different echo response, as indicated with P(t=t0+dt).

Figure 3:
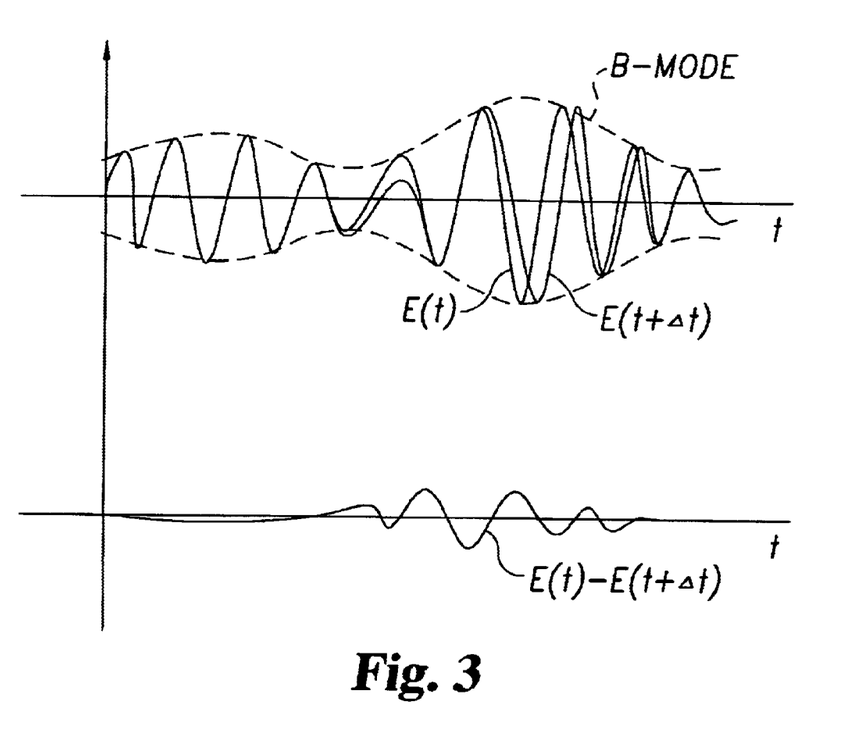
FIG. 3 shows superposed echo signals E(t) and E(t+dt) and the difference E(t)–E(t+dt).
Figure 4:
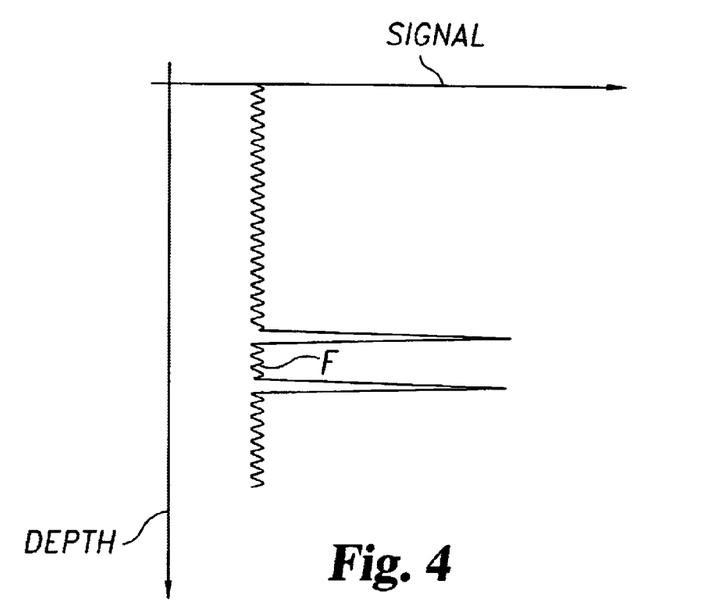
FIG. 4 shows the amplitude of the difference signal in the condition of FIG. 2.

This situation is also schematically shown in FIG. 3. The first graph represents the two superposed signals En(t0) and En(t0+dt). In the first signal portion, the two signals are superposed in a substantially congruent manner whereas, in the portion referred to the flow, i.e. in the signal portion whose contribution derives from the reflection by particles, particularly by red blood cells, the two signals are offset from each other.

The bottom graph of FIG. 3 shows the difference signal, which is equal to zero or substantially equal to zero in the zones in which the two signals En(t0) and En(t0+dt) are congruent (stationary tissues) and is other than zero in the zone corresponding to the blood flow.

Said subtraction is performed in real time in a unit 6 of the processing circuit. The method allows to obtain a high sensitivity to even very little and relatively slow movements. Such sensitivity is a considerable advantage in certain conditions and for certain types of examination. In fact, the method according to the invention can provide accurate and clear ultrasonic images, for instance of intraoperative instruments while the latter are positioned or moved inside the body. These instruments are generally hyperechogenic structures, hence they generate problems in other ultrasonic imaging methods.

Moreover, the considerable sensitivity to micromovements of the method according to the invention provides diagnostically valid ultrasonic images of biological structures, such as calcifications or particularly breast cancer formations.

Nevertheless, when performing imaging of spontaneous flows, such as blood flows, which have a strongly anechogenic character and are surrounded by echogenic and hyperechogenic tissues, such as vessel walls, the high sensitivity of the method may be a problem. In this case, any micromovement of the probe with respect to the body may generate non-zero contributions by echogenic and hyperechogenic tissues to the difference signal. These contributions have such an intensity that they dazzle the contributions to the difference signal by spontaneous flows.

In this case, the method according to the invention allows to define a maximum signal threshold above which the contributions to the difference signal are strongly attenuated or set to zero.

Such threshold is determined by the well-known B-Mode echo signal processing technique. The signals En(t) are checked for the presence of peaks, due to hyperechogenic and echogenic and anechogenic structures. The maximum threshold of the difference signal is set below the intensity of the signals En(t) in the portion corresponding to echogenic and hyperechogenic tissues.

Figure 5:
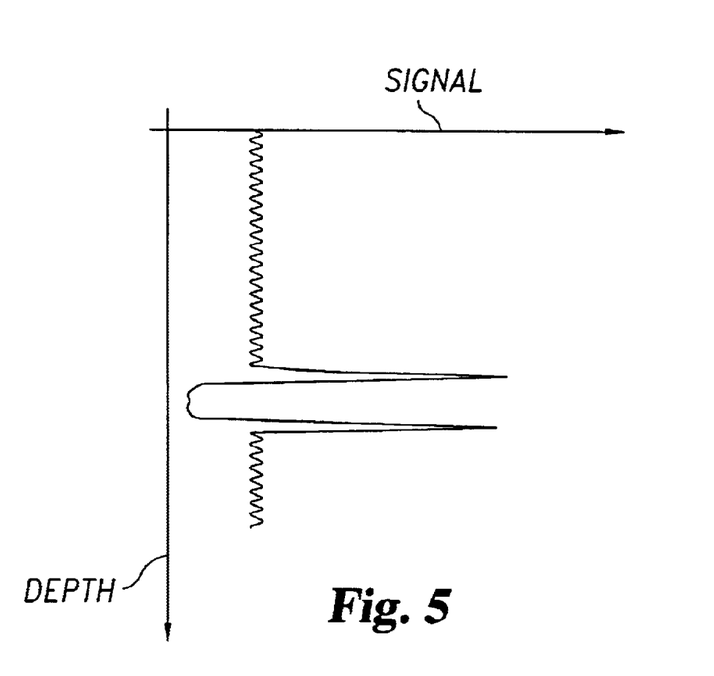
FIG. 5 shows the amplitude of the signal obtained by the conventional B-Mode method.
Figure 6:
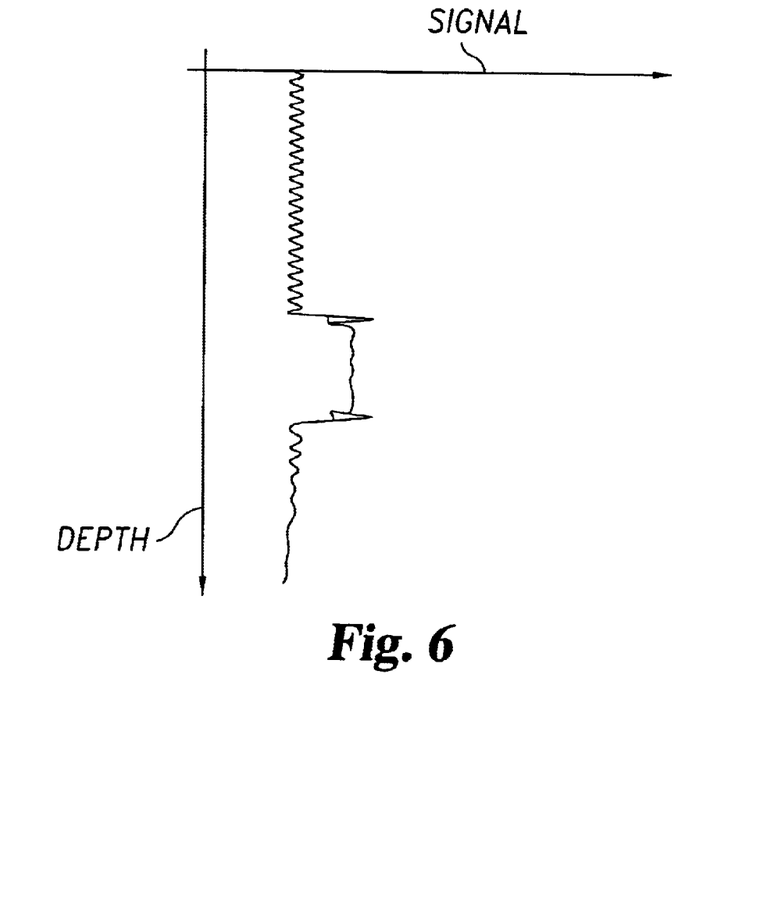
FIG. 6 shows the signal obtained with the help of the threshold for filtering artifacts due to micromovements of hyperechogenic and echogenic structures and of the partial difference between the two signals e(t) and E(t+dt).

The intensity of the signal En(t) relative to the transducer Tn along the axis of view or propagation and according to B-Mode processing is shown in FIG. 5. FIG. 6 shows the situation of a micromovement of the probe 1 relative to the body, wherefore the level of the difference signal Diff in the stationary tissue zones is substantially similar to or higher than that of the signal in the zones corresponding to the spontaneous flow. The two peaks correspond to the hyperechogenic walls of the vessel as shown in FIG. 2.

The graphs show how the level of the signal Diff in the flow zone denoted as F is similar to the level of the signal Diff., in the stationary tissue zone when relative micromovements between the probe 1 and said tissues occur. However, in the B-Mode processing method, the signal level relative to the flow is considerably lower than the level of the signals relative to the stationary tissues.

Typically, the B-Mode processing signal provides intensities of about 80–90 dB for the peaks of vessel walls and of about 40 dB for the areas of stationary echogenic tissues. Hence, in these conditions, a maximum threshold of about 15 to 30 dB may be set for the signal Diff. Therefore, when micromovements occur between the probe and the tissues or between different tissues, the contributions to the signal Diff. higher than 15 to 30 dB are automatically excluded or set to zero or attenuated.

Hence, the signal Diff has the same aspect as that indicated in FIG. 6.

According to a further variant, a minimum threshold value may be also determined to filter the signal Diff. when desired.

According to a further characteristic of the invention, advantages may be obtained from not performing a full subtraction between two successive signals En(t0)−En(t0+dt), and limiting suppression of the portions of signal generated by stationary tissue zones.

In this case, the difference signal Diff. is obtained by the following processing:

$$Diff = aEn(t0) - (1-a)En(t0+dt)$$

The weight "a" allows to keep a certain intensity of the signal Diff. even at the stationary tissue zones and in this case, each image line Ln also contains visual information about the tissues surrounding the flow F.

FIG. 6 shows this situation. In the signal portions deriving from the stationary tissues, the signal level is greater than zero, but lower than the signal level in the flow zones F.

It has to be noted how, in the method according to the invention, processing occurs on RF signals in the time domain and before transformation of signals En in pure image signals.

Figure 7:
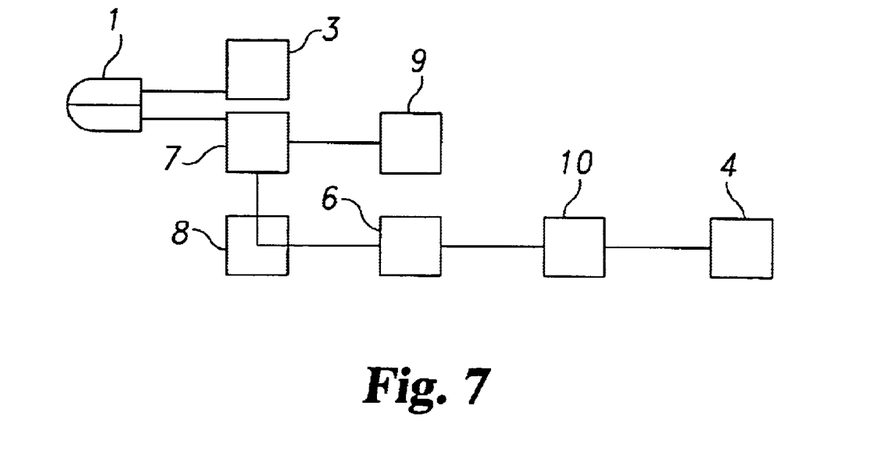
FIG. 7 is a simplified diagram of the apparatus.

Hence, the apparatus according to the invention, as shown in FIG. 7 includes a "B-Mode" processor of signals En, denoted with numeral 9, with a unit 7 for sampling the signals En and a unit for determining the signal Diff. denoted with numeral 8, as well as a unit for determining the maximum threshold, denoted with numeral 6. The unit 10 consists of a conventional unit for processing echo signals into image signals transmitted to the display 4. It has to be noted that the diagram of the apparatus does not show the units for performing the conventional steps of all the processing units of ultrasound machines, which are not relevant for the present invention and do not form the subject thereof, and are known in prior art. Obviously, these circuits or methods are intended to be provided in combination with the method of the invention.

When the interest of the imaging lies in evaluating the position or displacement of an intraoperative surgical utensil the above described technique may be applied without any difference as the one that the part of the difference signal which is used for reconstructing the image is the one lying above the maximum threshold of the difference signal. In this case this threshold has to be considered as a minimum intensity threshold and is value is determined in relation of the tipical reflection signal intensity of the kind of tissue, body or structure to be imaged.

It is possible to set at the same time different thresholds, as for example one maximum and one minimum threshold, thus defining a window between them. According to the object of imaging, the contribution above the maximum threshold or the contribution below the minimum threshold or the contribution within the threshold window of the difference signals may be used for reconstructing an image. Furthermore the contribution relating to the different parts of the difference signals as discriminated by the thresholds may be coupled to form a combination image. In this case each contribution may be affected by a weight for trimming their relevance in the reconstructed image.

Also in the case of imaging hyperechogenic structures or bodies or tissues the image obtained from the difference signals may be combined with a conventional b-mode image by providing the two echo signals which are subtracted one from the other by a weight such as the contribution of stationary tissues is not completely eliminated from the difference signals to be used for reconstructing the image with the effect already described above for the case of imaging not echogenic spontaneous physiological flows, such as blood flows or the like.

It is also interesting to consider a surprising effect of the method and apparatus according to the invention. Due to the high sensitivity to moving tissues relatively to the probe, particularly in case of micro displacements, the method and the apparatus according to the invention allow to scan images of biological structures which are particularly difficult to be imaged with ultrasound devices. This is the case for example of calcifications. In this case natural micromovements of the calcifications due to natural relative movements occurring between probe and body of the patient or to spontaneous or induced movements of the organ or body region in where the calcifications are located allow to have an echo contribution from the calcifications from which a valid image of it may be reconstructed. The method according to the invention achieves this aim again by using echo signal parts which would be rejected according to the actual techniques.

As it is clear from the above description, the method according to the invention can provide ultrasonic images of spontaneous flows without using raiopaque agents. However, the method is also applicable in combination with contrast agents without requiring substantial changes.

The only change which may be required consists in determining thresholds for filtering the signal Diff., since the contribution to the echo signal by the flow when using contrast agents reaches very high levels, higher than those of the hyperechogenic tissues.

In this case, instead of a maximum threshold for the signal Diff., a minimum threshold is set with the help of B-Mode processed signals, below which the signal Diff. is to be set to zero or attenuated.

What is claimed is:

1. A method for ultrasonic imaging, particularly of moving bodies, comprising the following steps:
   periodically emitting ultrasonic pulses along a predetermined view line and with a predetermined repetition rate through one or more transducers;
   receiving echoes produced by first and second objects and transforming them into echo signals;
   processing the echo signals for extracting information therefrom and for generating an image based on such information,
   characterized by the following additional steps:
   determining real time vector difference signals between echo signals of two pulses successively emitted at predetermined time intervals from said first and second objects;
   applying a threshold level to said difference signals to form first and second signal level regions such that the difference signal from said one of said objects substantially falls within said first region and said difference signal from said other object substantially falls within said second region; and
   attenuating the level of said echo signals from said object whose difference signal substantially falls within said first region in order to enhance the image of said other object.

2. A method as claimed in claim 1, characterized in that a non linear filtering of the difference signal between two successive echo signals is performed to retain for reconstructing the image high intensity components of the difference signal or low intensity component of the difference signal for alternatively or parallel neutralize signals due to non echogenic regions and image bodies, tissues or structures having echogenic or hyperechogenic responses and executing micromovements or displacements relating to the probe or neutralize signal flashes generated by relative micromovements between the probe and the echogenic or hyperechogenic tissues surrounding non echogenic bodies like physiologic flows.

3. A method as claim in claim 2, characterized in that the portions of the difference signal between two successive echo signals exceeding the maximum threshold are set to zero or attenuated below a predetermined value or according to a predetermined attenuation factor, whereas the portions of the signal below the maximum threshold are retained and transformed into images.

4. A method as claimed in claim 2, characterized in that the portions of the difference signal between two successive echo signals below the maximum threshold are set to zero or attenuated below a predetermined value or according to a predetermined attenuation factor, whereas the portions of the signal above the maximum threshold are retained and transformed into images.

5. A method as claimed in claim 2, characterized in that it provides partial subtraction of the second echo signal from the first echo signal, by appropriate weighting, to attenuate without completely suppressing the contribution to the difference signal by stationary tissues, so that a combination of the flow image with an attenuated image of the tissues surrounding the flow may be obtained.

6. A method as claimed in claim 1 or 2, characterized in that a maximum and/or minimum threshold is set for filtering the difference signal between two successive echo signals, the difference signal part above and or below and or within said thresholds being used for reconstructing the image, while the other part of the signal is at least attenuated or set to zero.

7. A method as claimed in claim 6, characterized in that filtering is performed by using two thresholds, a minimum and a maximum threshold, on echo signals being determined, with the B-Mode method, as signal levels for stationary tissues and flow and/or for echogenic or hyperechogenic materials executing micromovements or displacements relatively to the probe.

8. A method as claimed in claim 1, characterized in that a minimum threshold is also defined for the difference signal between two successive echoes, below which the signal is set to zero or attenuated, while the part of the signal within the minimum and maximum threshold is alternatively attenuated or set to zero, partially attenuated and retained to reconstruct the image in combination with the part of the signal above the maximum threshold or retained without attenuation for reconstructing the image alone or in combination with the part of the signal above the maximum threshold.

9. A method according to claim 8, characterized in that the signal parts above the maximum threshold, below the minimum threshold and between the two said thresholds is retained for imaging being evaluated in parallel and independently to each other and combined with different weights to form a combined image.

10. A method according to claim 1, characterized in that a minimum threshold is also defined for the difference signal between two successive echoes, below which the signal is retained to reconstruct the image, while the part of the signal within the minimum and maximum threshold is alternatively attenuated or set to zero, partially attenuated and retained to reconstruct the image in combination with the part of the signal below the minimum threshold or retained without attenuation for reconstructing the image alone or in combination with the part of the signal below the minimum threshold, while above the maximum threshold the signal is attenuated or set to zero.

11. A method as claimed in claim 1, characterized in that its use is provided in combination with the introduction of contrast agents in spontaneous flow.

12. A method as claimed in claim 11, characterized in that a minimum threshold is defined for the difference signal between two successive echoes, below which the difference signal is set to zero or strongly attenuated.

13. A method as claimed in claim 1, characterized in that it is used for detecting displacements of invasive surgical instruments, such as microinstruments, intraoperative probes, and needles.

14. A method as claim in claim 1, characterized in that it is used for the detection of calcifications or similar structures.

15. An apparatus for ultrasonic imaging, comprising:
   a probe for emitting RF ultrasonic pulses, generally consisting of a set of transducers aligned on at least one line;
   transducers for receiving the echo signals reflected by a first object and a second object while the illuminating ultrasonic pulses propagate therein;
   processing means, including means for generating an image from said echo signals received from said first and second objects;
   means for determining difference signals between two received echo signals from said first and second objects;
   means for applying a threshold level to said difference signals to form first and second signal level regions such that the difference signal from one of said objects substantially falls within said first region and said difference signal from said other object substantially falls within said second region; and means for attenuating the level of said echo signals from said object whose difference signal substantially falls within said first region in order to enhance the image of said other object.

16. An apparatus as claimed in claim 15, characterized in that it includes a unit for generating a maximum threshold for the difference signal and means for discriminating the parts of the signal above and below the threshold as well as means for attenuating, setting to zero or retaining one of the two parts of the signal discriminated by the threshold.

17. An apparatus as claimed in claim 15, characterized in that it includes a unit for generating a minimum threshold for the difference signal and means for discriminating the parts of the signal above and below the threshold as well as means for attenuating, setting to zero or retaining one of the two parts of the signal discriminated by the threshold.

18. An apparatus according to claim 15, characterized in that it includes a unit for generating at least a maximum and at least a minimum threshold for the difference signal and means for discriminating the parts of the signal in relation to the thresholds as well as means for attenuating, setting to zero or retaining one or more of the parts of the signal discriminated by the thresholds.

19. An apparatus as claimed in claim 15, characterized in that it includes a "B-Mode" echo signal processing unit.

20. An apparatus as claimed in claim 15, characterized in that it includes means for weighting echo signals to be subtracted, so that a signal of a certain predetermined level may be obtained even with the contributions of stationary tissues.

21. An apparatus as claimed in claim 15, characterized in that it is used for detecting displacements of invasive surgical instruments, such as microinstruments, intraoperative probes, and needles.

22. An apparatus as claimed in claim 15, characterized in that it is used for the detection of calcifications or similar structures.

* * * * *